United States Patent [19]

Ray

[11] Patent Number: 4,610,243

[45] Date of Patent: Sep. 9, 1986

[54] MALLEABLE FORCE-FULCRUM RETRACTOR

[75] Inventor: Charles D. Ray, Deephaven, Minn.

[73] Assignee: Charles D. Ray, Ltd., Wayzata, Minn.

[21] Appl. No.: 731,025

[22] Filed: May 6, 1985

[51] Int. Cl.⁴ .............................................. A61B 1/00
[52] U.S. Cl. .................................................... 128/20
[58] Field of Search ......................................... 128/20

[56] References Cited

U.S. PATENT DOCUMENTS 3,542,015  11/1970  Steinman ............................... 128/20

OTHER PUBLICATIONS

*The Surgical Armamentarium*, American V. Mueller title page and p. 64, ©1980.

Primary Examiner—William H. Grieb
Attorney, Agent, or Firm—Williamson, Bains, Moore & Hansen

[57] ABSTRACT

A Taylor-type force-fulcrum retractor has a broad malleable band which is readily shaped by hand to fit any situation and yet holds that shape against forces that may be applied to pull the muscles away from the center of an incision. The force-fulcrum retractor is particularly useful in spinal surgery and may have a claw-like spike or spikes which penetrate the surface of a bone within the incision to establish an extraordinarily secure fulcrum.

20 Claims, 4 Drawing Figures

MALLEABLE FORCE-FULCRUM RETRACTOR

FIELD OF THE INVENTION

The invention concerns a force-fulcrum retractor similar to the Taylor retractor. The invention also concerns a force-fulcrum retractor, the fulcrum point or points of which are novel.

BACKGROUND ART

The majority of retractors used in spinal surgery are hand held or self retaining. A few of these are force-fulcrum retractors comprising a broad metal band having at one end a fulcrum point or points which are inserted deep into the incision and lodged against bone. After such a retractor is inserted to establish a fulcrum, a weight or counterforce is applied by attaching a gauze strip to the free end of the retractor and tying the strip either to the operating table or to a weight hanging over the edge of the table, thus pulling the muscles and related tissue away from the center of the incision to expose the deep tissues such as spinal structures.

The most commonly used force-fulcrum retractor is the flat-bladed Taylor retractor which has a single, somewhat blunted tooth as its fulcrum point. Its band is curved so that the central portion rests substantially flat against the patient's back. Usually its tooth extends from the end of the retractor at an angle of about 30° in the direction opposite to the direction of the curve. To accommodate various back thicknesses, suppliers typically stock pairs of Taylor retractors, which have differing lengths between their central curves and their teeth. Taylor retractors of almost identical construction are available from a number of sources, e.g., R-1080 and R-1085 of Ruggles Corp., Boston, Mass.; 2580-10 and 2580-12 of DePuy, Warsaw, Ind.; and 11-0621 and 11-0622 of Richards, Inc., Memphis, Tenn. A force-fulcrum retractor which like the Taylor comprises a centrally curved broad metal band but has two teeth is the Viboch iliac graft retractor 11-1171 of Richards, Inc. A rake retractor (which is not a force-fulcrum retractor) often has more than two teeth such as the Hibbs retractor 2577-00 of DePuy.

DISCLOSURE OF INVENTION

The invention provides a force-fulcrum retractor which is similar in shape to the flat-bladed Taylor retractor but is more versatile and more convenient to use. Furthermore, preferred embodiments of the novel force-fulcrum retractor are somewhat less likely to cause damage while more reliably holding the muscles and related tissue away from the center of the incision. Like the Taylor retractor, that of the present invention comprises a broad band, preferably a metal band, having at one end at least one point to establish a fulcrum within a surgical incision. The novel force-fulcrum retractor differs from the Taylor retractor in that the metal or other material of the band is sufficiently malleable that the band can readily be bent by hand to a desired shape while being sufficiently stiff to hold that shape against a retractile force applied to the other end of the band to pull the muscles away from the center of the incision.

Because the retractile force needed to pull the muscles away from the center of the incision is usually quite low, a one kg weight usually being sufficient, the material of the band may be selected to withstand that force. However, the material of the band preferably holds its shape against a weight of at least 2 kg applied to said other end of the band.

Because of its malleability, the novel force-fulcrum retractor can be shaped to reach a particular depth when placed in an incision, removed, and easily reshaped as the surgeon requires without the need for any instrument other than the surgeon's gloved hands. If left as bent when sterilized and stored, only minor reshaping should be needed for the next operation.

Like the Taylor retractor, the fulcrum of the novel force-fulcrum retractor may have at least one tooth formed in said one end of the malleable band. However, when the novel band has only one fulcrum point, that point preferably is a rigid spike fixed to and projecting beyond said one end of the band. Preferably the spike has a circular cross section and is in the form of a claw which is gently curved so that its point extends at an acute angle with the said one end of the band.

To fix a spike to the band, the face of the spike which is to rest against the band is preferably first machined to form a flat extending almost to the diameter of the spike. When the spike is then fixed to the band by welding, sweat-soldering, or brazing its flat to the band, there are no voids or interstices to trap tissue fluids or debris.

At the fifth lumbar level and further caudad along the sacrum, neither a one- nor a two-toothed retractor is practical or stable in most cases, since an appropriate ridge of prominence of bone cannot be found against which to lodge the teeth. For good stability, the retractor should have one or more sharp spikes, preferably claws, the number and spacing of which depends upon the bony structures, e.g., the distance between the posterior iliac spines. In general, two rather widely spaced spikes are desirable for deeper incisions, while a relatively narrow force-fulcrum retractor having only a single spike may be more desirable for a shallow, and hence often narrow, incision. In any case, the spiked tip is gently driven by hand into the sacrum or wedged into the sacro-iliac joint lateral to posterior sacral foraminae. The spiked retractors are also quite practical to be used during exposures for partial, lateral take-down of a fusion. One must be careful, however, in placing so that a spike does not pass into a sacral foramen.

Whether or not the fulcrum of the novel force-fulcrum retractor has one or more teeth or spikes, each tooth or spike preferably extends from the end of the malleable band at an acute angle, because this provides better assurance against slippage. Preferably that acute angle is at least 10° but not more than 40°.

While the spike should have a sharp apex, it should be tapered to a thickness beyond the end of the band that will not readily penetrate a bone so that a small clearance remains between the bone and the end of the band, thus avoiding abrasion of the bone when the force-fulcrum retractor is pulled back. On the other hand, that clearance should be small so that muscles and tissue close to the bone are drawn back. To assure this, the spike may have a thickness of at least 2 mm (preferably about 3 mm) except at the apex, and a single spike should not extend more than about 1.25 cm beyond the end of the band. When there are two spikes, a lesser degree of penetration is needed, and they preferably extend no more than 1 cm beyond the end of the band. Whether there is one or more spikes, each spike should extend at least 0.5 cm beyond the end of the band to allow sufficient penetration into the bone while still leaving a small clearance between the bone and the end of the band.

Another preferred force-fulcrum retractor of the invention has a pair of somewhat blunted teeth which can be hooked laterally around a pedicle or other structure in a spinal operation. The notch between the two teeth may be placed just lateral to a facet joint, thus providing a very stable, yet easily movable access to the surgical target. Care should be taken not to apply a force that would break a facet joint. Usually a weight of 2 kg can be attached to the free end of the force-fulcrum retractor without any danger.

In another application for a 2-toothed malleable force-fulcrum retractor involving surgical approaches from a far-lateral access (between the spinal erector group and the quadratus lumborum, the paralateral approach), the retractor tip is placed medial to the facet, prying upward (dorsal) with the attached, weighted gauze strip passed over the opposite side of the operating table.

The novel force-fulcrum retractor may be furnished in several widths for use in incisions of various sizes. A useful set of the novel retractors includes:
 a force-fulcrum retractor having a single claw and a width of 1.75 cm,
 a second retractor having two claws and a width of 3 cm,
 a third retractor having two claws and a width of 4 cm,
 a fourth retractor having two teeth and a width of 1.75 cm,
 a fifth retractor having two teeth and a width of 3 cm, and
 a sixth retractor having two teeth and a width of 4 cm.

Also proving to be useful experimentally is a seventh retractor having two claws and a width of 5 cm.

Each of these force-fulcrum retractors may be annealed 304 soft stainless steel having a thickness of about 1 mm. While a harder metal would permit the band of the retractor to be thinner, the relatively sharper edges of the retractor would create a danger of trauma to tissues at the edges of the retractor. A softer metal would allow the force-fulcrum retractor to have greater thickness, but the resulting increase in weight would involve increased danger of injury to the patient.

THE DRAWING

Figure 1:
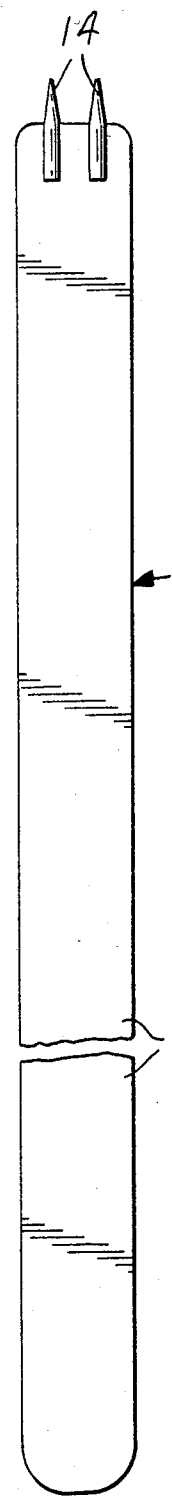
FIG. 1 is a plan view of a preferred force-fulcrum retractor of the invention.
Figure 3:
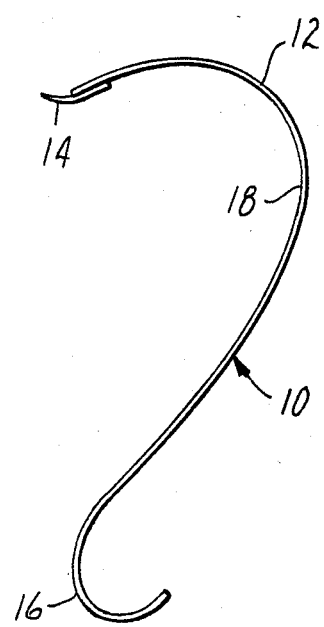
FIG. 3 is an edge view of the retractor shown in FIG. 1.

The force-fulcrum retractor 10 shown in FIGS. 1 and 3 has a broad malleable metal band 12, to one end of which are welded a pair of rigid metal spikes 14 which together can provide a fulcrum point. Each of the spikes 14 has a circular cross section and, as can be seen in FIG. 3, is shaped like a claw. The apex of the claw extends at an angle of about 30° to the end of the metal band 12. The opposite free end of the band has a curve or hook 16 to which a strip of gauze may be tied in order to suspend a weight. Upon inserting the spikes 14 deep into a spinal incision, such a weight pulls the muscles and other tissue away from the center of the incision while the central portion 18 of the band rests against the patient's back.

Figure 2:
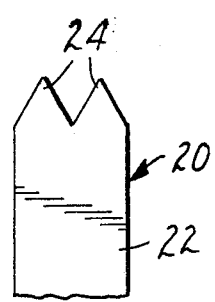
FIG. 2 is a fragmentary plan view of another preferred force-fulcrum retractor of the invention.
Figure 4:
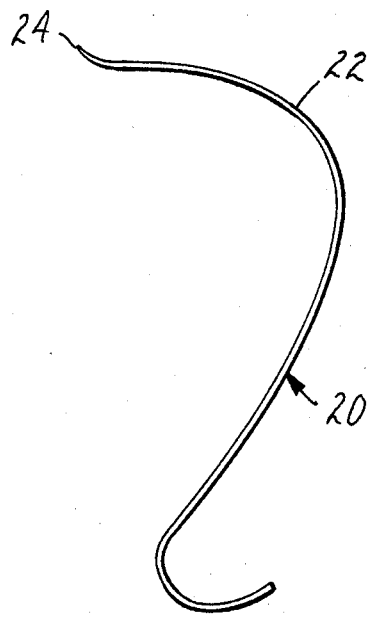
FIG. 4 is an edge view of the retractor shown in FIG. 2.

The force-fulcrum retractor 20 shown in FIGS. 2 and 4 has a broad malleable metal band 22, one end of which is formed with a pair of teeth 24. As can be seen in FIG. 4, each of the teeth is curved, and its tip extends at an angle of about 30° to the end of the metal band 22.

The malleable metal bands may be marketed either flat or shaped as shown in FIGS. 3 and 4. If pre-shaped, the surgeon need to make only a minor adjustment to accommodate the first patient. However, it might be easier to ship and store flat force-fulcrum retractors.

Because the malleable band of a force-fulcrum retractor of the invention can be shaped as desired, surgeons will devise shapes quite different from those illustrated. For example, I have recently reshaped the metal band 12 of the retractor 10 to form an S-shaped curve in the half of its length closer to the claw 14 in addition to the reverse S in the other half as seen in FIG. 3. This provided deeper retraction to enhance access to pelvic bone structure for harvesting a bone graft.

I claim:

1. Force-fulcrum retractor comprising a broad band having at one end at least one point to establish a fulcrum within a surgical incision, wherein the improvement comprises:
 the material of the band is sufficiently malleable so that the band can readily be bent by hand to a desired shape while being sufficiently stiff to hold that shape against a retractile force applied to the other end of the band to pull the muscles away from the center of the incision.

2. Force-fulcrum retractor as defined in claim 1 wherein said fulcrum point is at least one tooth formed in said one end of the band.

3. Force-fulcrum retractor as defined in claim 2 wherein said fulcrum point is a pair of teeth.

4. Force-fulcrum retractor as defined in claim 1 wherein said point is a rigid spike fixed to and projecting beyond said one end of the band.

5. Force-fulcrum retractor as defined in claim 4 wherein the spike has a circular cross section and is in the form of a claw which is is gently curved so that its point extends at an acute angle with the said one end of the band.

6. Force-fulcrum retractor as defined in claim 5 wherein each spike is formed with a flat which is fixed to the band.

7. Force-fulcrum retractor as defined in claim 6 wherein each spike projects from 0.5 to 1.25 cm beyond the end of the band.

8. Force-fulcrum retractor as defined in claim 7 wherein each spike has a diameter of at least 2 mm except at the apex and projects from 0.5 to 1.25 cm beyond the end of the band.

9. Force-fulcrum retractor as defined in claim 5 having a single spike.

10. Force-fulcrum retractor as defined in claim 5 having a pair of spikes.

11. Force-fulcrum retractor as defined in claim 1 wherein the material of said band is soft stainless steel.

12. Force-fulcrum retractor as defined in claim 11 wherein the thickness of the band is approximately 1 mm.

13. Force-fulcrum retractor as defined in claim 1 wherein the material of the band is selected so that when the retractor is bent to a curved shape and its fulcrum point is inserted into an incision, a weight of 2 kg suspended from the free end of the retractor does not change its shape.

14. Force-fulcrum retractor comprising a broad band having at one-end at least one point to establish a fulcrum within a surgical incision, wherein the improvement comprises:

said point is a rigid spike fixed to and projecting beyond said one end of the band, and the spike has a diameter of at least 2 mm except at the apex and extends not more than 1.25 cm beyond the end of the band.

15. Force-fulcrum retractor as defined in claim 14 wherein said spike is formed with a flat which is fixed to the band.

16. Force-fulcrum retractor as defined in claim 14 wherein said spike has a circular cross section and is in the form of a claw which is gently curved so that its point extends at an acute angle with the said one end of the band.

17. Force-fulcrum retractor comprising a broad band having at one end at least one point to establish a fulcrum within a surgical incision, wherein the improvement comprises:

said point is a rigid spike fixed to and projecting beyond said one end of the band, which spike has a circular cross section and is in the form of a claw which is gently curved so that its point extends at an acute angle with the said one end of the band.

18. Force-fulcrum retractor as defined in claim 17 wherein each spike is formed with a flat which is fixed to the band by a technique selected from welding, sweat-soldering, and brazing.

19. Force-fulcrum retractor as defined in claim 18 wherein each spike projects from 0.5 to 1.25 cm beyond the end of the band.

20. Force-fulcrum retractor as defined in claim 19 wherein each spike has a diameter of at least 2 mm except at the apex.

* * * * *